US 9,114,164 B2

(12) United States Patent
Corr et al.

(10) Patent No.: US 9,114,164 B2
(45) Date of Patent: Aug. 25, 2015

(54) COMPOSITIONS COMPRISING SALBUTAMOL SULPHATE

(71) Applicant: MEXICHEM AMANCO HOLDING S.A. DE C.V., Viveros del Rio, Tlalnepantla (MX)

(72) Inventors: Stuart Corr, Cheshire (GB); Timothy James Noakes, Flintshire (GB)

(73) Assignee: Mexichem Amanco Holding S.A. DE C.V., Viveros del Rio, Tlalnepantla (MX)

( * ) Notice: Subject to any disclaimer, the term of this patent is extended or adjusted under 35 U.S.C. 154(b) by 0 days.

(21) Appl. No.: 14/351,001

(22) PCT Filed: Oct. 12, 2012

(86) PCT No.: PCT/GB2012/052542
§ 371 (c)(1),
(2) Date: Apr. 10, 2014

(87) PCT Pub. No.: WO2013/054135
PCT Pub. Date: Apr. 18, 2013

(65) Prior Publication Data
US 2014/0286877 A1    Sep. 25, 2014

(30) Foreign Application Priority Data
Oct. 12, 2011 (GB) .................. 1117621.1

(51) Int. Cl.
*A61K 47/06* (2006.01)
*A61K 9/12* (2006.01)
*A61K 9/00* (2006.01)
*A61K 31/137* (2006.01)
*A61M 15/00* (2006.01)

(52) U.S. Cl.
CPC ............. *A61K 47/06* (2013.01); *A61K 9/008* (2013.01); *A61K 9/12* (2013.01); *A61K 9/124* (2013.01); *A61K 31/137* (2013.01); *A61M 15/002* (2013.01); *A61M 15/009* (2013.01)

(58) Field of Classification Search
None
See application file for complete search history.

(56) References Cited

U.S. PATENT DOCUMENTS 5,439,670 A    8/1995    Purewal et al.
6,103,266 A    8/2000    Tapolsky et al.
(Continued)

FOREIGN PATENT DOCUMENTS

CN    1296814 A    5/2001
CN    1389202 A    1/2003
(Continued)

OTHER PUBLICATIONS

Machine Translation of Chinese Publication No. CN1296814 A (A6 above) dated May 30, 2001.
(Continued)

*Primary Examiner* — Bethany Barham
*Assistant Examiner* — Barbara Frazier
(74) *Attorney, Agent, or Firm* — Brinks Gilson & Lione

(57) ABSTRACT

A surfactant-free pharmaceutical composition is described. The composition consists essentially of: (a) a drug component consisting of salbutamol sulphate; and (b) a propellant component consisting essentially of 1,1-difluoroethane (R-152a). A method for preparing the pharmaceutical composition is also described. The pharmaceutical composition can be delivered using a metered dose inhaler (MDI).

12 Claims, 1 Drawing Sheet

(56) References Cited

U.S. PATENT DOCUMENTS

| | | |
|---|---|---|
| 6,413,497 B1 | 7/2002 | Weil et al. |
| 6,475,467 B1 | 11/2002 | Keller et al. |
| 7,105,152 B1 | 9/2006 | Schultz et al. |
| 2007/0256685 A1* | 11/2007 | Mueller-Walz .......... 128/200.23 |

FOREIGN PATENT DOCUMENTS

| | | |
|---|---|---|
| EP | 0372777 A2 | 6/1990 |
| EP | 0653204 A2 | 5/1995 |
| EP | 0995434 A2 | 4/2000 |
| EP | 2072051 A1 | 6/2009 |
| GB | 2392915 A | 3/2004 |
| WO | WO 91/11173 A1 | 8/1991 |
| WO | WO 93/11747 | 6/1993 |
| WO | WO 96/19198 A1 | 6/1996 |
| WO | WO 96/32151 A1 | 10/1996 |
| WO | WO 99/16422 A1 | 4/1999 |
| WO | WO 99/65460 A2 | 12/1999 |
| WO | WO 01/43722 A2 | 6/2001 |
| WO | WO 2005/034911 A1 | 4/2005 |
| WO | WO 2005/034927 A2 | 4/2005 |
| WO | WO 2006/004646 A1 | 1/2006 |
| WO | WO 2007/020204 A2 | 2/2007 |
| WO | WO 2011/023734 A1 | 3/2011 |

OTHER PUBLICATIONS

PCT International Search Report for corresponding International Patent Application No. PCT/GB2012/052542 dated Feb. 11, 2013.
PCT Written Opinion for corresponding International Patent Application No. PCT/GB2012/052542 dated Apr. 12, 2014.
Noakes, T. "Medical Aerosol Propellants," *J. Fluorine Chem.*, 2002, 118, 35-45.
Machine Translation of the Chinese Publication No. CN1389202 A dated Jul. 15, 2015.

* cited by examiner

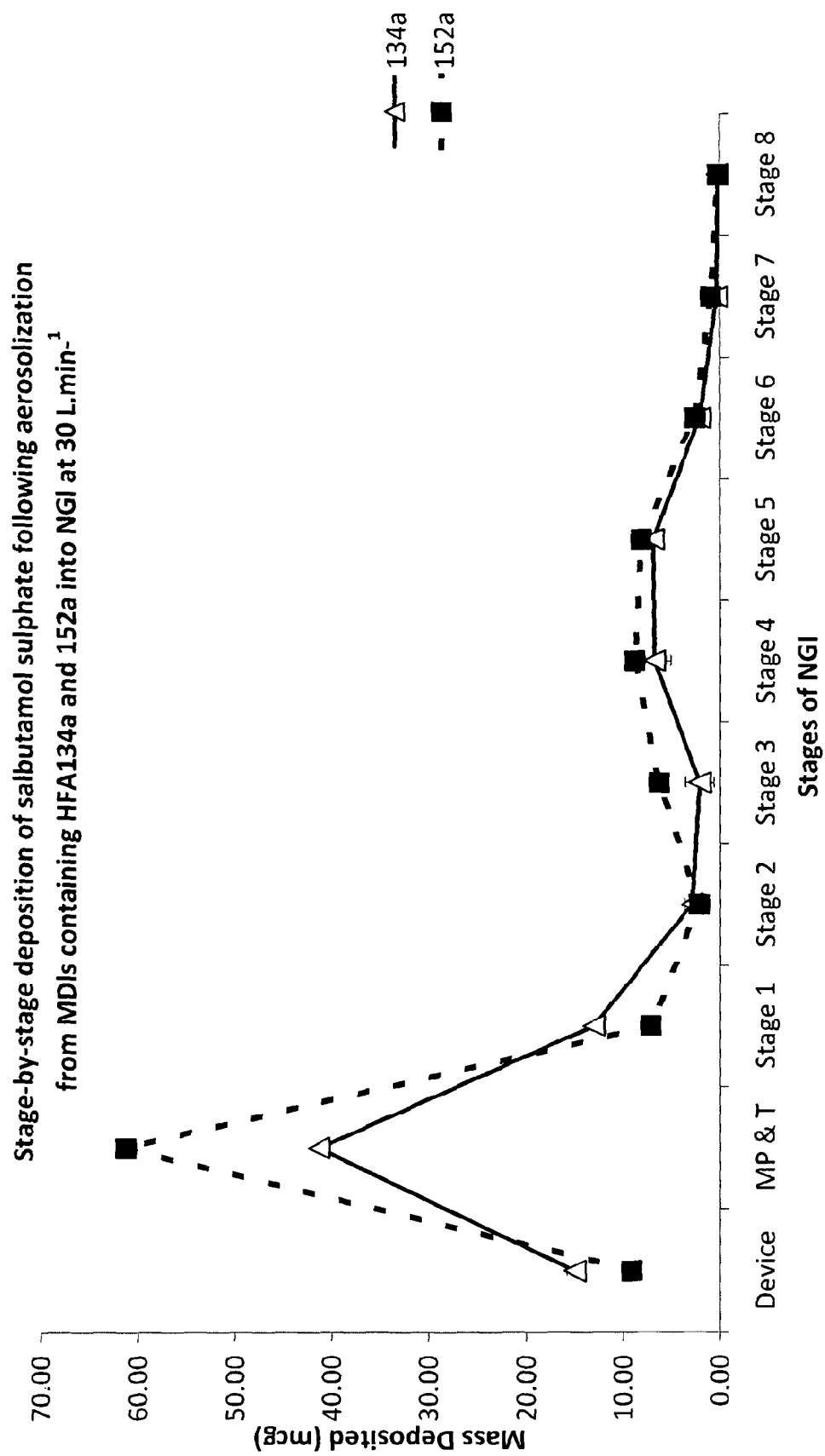

COMPOSITIONS COMPRISING SALBUTAMOL SULPHATE

CROSS-REFERENCE TO RELATED APPLICATIONS

This application is the U.S. National Phase under 35 U.S.C. §371 of International Patent Application No. PCT/GB2012/052542, filed Oct. 12, 2012, designating the United States and published in English on Apr. 18, 2013, as WO 2013/054135, which claims priority to United Kingdom Application No. 1117621.1, filed Oct. 12, 2011, which is incorporated by reference in its entirety.

FIELD

The present invention relates to a composition that is suitable for delivering salbutamol sulphate, especially from a pressurised aerosol container using a metered dose inhaler (MDI).

BACKGROUND

MDIs are the most significant type of inhalation drug delivery system and are well known to those skilled in the art. They are designed to deliver, on demand, a discrete and accurate amount of a drug to the respiratory tract of a patient using a liquefied propellant in which the drug is dissolved, suspended or dispersed. The design and operation of MDIs is described in many standard textbooks and in the patent literature. They all comprise a pressurised container that holds the drug formulation, a nozzle and a valve assembly that is capable of dispensing a controlled quantity of the drug through the nozzle when it is activated. All of these components are typically located in a housing that is equipped with a mouth piece. The drug formulation will comprise a propellant, in which the drug is dissolved, suspended or dispersed, and may contain other materials such as polar excipients, surfactants and preservatives.

In order for a propellant to function satisfactorily in MDIs, it needs to have a number of properties. These include an appropriate boiling point and vapour pressure so that it can be liquefied in a closed container at room temperature but develop a high enough pressure when the MDI is activated to deliver the drug as an atomised formulation even at low ambient temperatures. Further, the propellant should be of low acute and chronic toxicity and have a high cardiac sensitisation threshold. It should have a high degree of chemical stability in contact with the drug, the container and the metallic and non-metallic components of the MDI device, and have a low propensity to extract low molecular weight substances from any elastomeric materials in the MDI device. The propellant should also be capable of maintaining the drug in a homogeneous solution, in a stable suspension or in a stable dispersion for a sufficient time to permit reproducible delivery of the drug in use. When the drug is in suspension in the propellant, the density of the liquid propellant is desirably similar to that of the solid drug in order to avoid rapid sinking or floating of the drug particles in the liquid. Finally, the propellant should not present a significant flammability risk to the patient in use. In particular, it should form a non-flammable or low flammability mixture when mixed with air in the respiratory tract.

Dichlorodifluoromethane (R-12) possesses a suitable combination of properties and was for many years the most widely used MDI propellant, often blended with trichlorofluoromethane (R-11). Due to international concern that fully and partially halogenated chlorofluorocarbons (CFCs), such as dichlorodifluoromethane and trichlorofluoromethane, were damaging the earth's protective ozone layer, many countries entered into an agreement, the Montreal Protocol, stipulating that their manufacture and use should be severely restricted and eventually phased out completely. Dichlorodifluoromethane and trichlorofluoromethane were phased out for refrigeration use in the 1990's, but are still used in small quantities in the MDI sector as a result of an essential use exemption in the Montreal Protocol.

1,1,1,2-tetrafluoroethane (R-134a) was introduced as a replacement refrigerant and MDI propellant for R-12. 1,1,1,2,3,3,3-heptafluoropropane (R-227ea) was also introduced as a replacement for dichlorotetrafluoroethane (R-114) in the MDI sector and is sometimes blended with R-134a for this application.

Although R-134a and R-227ea have low ozone depletion potentials (ODPs), they have global warming potentials (GWPs), 1430 and 3220 respectively, that are now considered to be too high by some regulatory bodies, especially for dispersive uses when they are released into the atmosphere.

One industrial area that has received particular attention recently has been the automotive air-conditioning sector where the use of R-134a has come under regulatory control as a result of the European F-Gas Regulations. Industry is developing a number of possible alternatives to R-134a in automotive air conditioning and other applications that have a low greenhouse warming potential (GWP) as well as a low ozone depletion potential (ODP). Many of these alternatives include hydrofluoropropenes, especially the tetrafluoropropenes, such as 2,3,3,3-tetrafluoropropene (R-1234yf) and 1,3,3,3-tetrafluoropropene (R-1234ze).

Although the proposed alternatives to R-134a have a low GWP, the toxicological status of many of the components, such as certain of the fluoropropenes, is unclear and they are unlikely to be acceptable for use in the MDI sector for many years, if at all.

There are also other problems with R-134a and R-227ea. Most pharmaceutical actives for treating respiratory disorders, such as asthma, tend not to dissolve well in either R-134a or R-227ea and have to be handled as suspensions in the propellant. Drug suspensions give rise to a number of problems, such as nozzle blockage, agglomeration and sedimentation, the latter problem making it essential to shake the MDI thoroughly before use to ensure that the drug is evenly distributed in the propellant. Furthermore, if the pharmaceutical active settles quickly following re-suspension in the propellant, as is often the case, then the propellant/drug composition must be delivered from the MDI shortly after shaking in order to ensure that the dose that is delivered contains an effective concentration of the pharmaceutical active.

The problem of poorly dissolving drugs has been addressed by including a polar excipient in the composition which either helps to dissolve the drug to form a solution or else enhances wetting of suspended drug particles to yield a better dispersed and more stable suspension. A preferred polar excipient is ethanol. However, the use of large amounts of ethanol can tend to result in a coarse spray having droplet sizes that are too large for acceptable penetration into the deep bronchiole passages of the lung. Further, high levels of ethanol can have unacceptable irritancy to the mouth and throat, especially with younger users. Clearly it would be advantageous to reduce the amount of ethanol that is required to produce an acceptable formulation. It would be better still if the use of ethanol could be avoided altogether.

Surfactants have also been included in some formulations that include drugs that are either insoluble or only sparingly soluble in the propellant, as these can also help to produce a more stable suspension. However, surfactants are not liked and it would also be beneficial to form a stable suspension without the use of a surfactant.

There is a need for a MDI aerosol formulation that has a reduced GWP in comparison with R-134a and R-227ea, that has acceptable flammability and toxicity performance, which forms stable suspensions with salbutamol sulphate and that has reduced irritancy.

SUMMARY

According to a first aspect of the present invention, there is provided a surfactant-free pharmaceutical composition consisting essentially of:
 a drug component consisting of salbutamol sulphate; and
 a propellant component consisting essentially of 1,1-difluoroethane (R-152a).

The pharmaceutical composition of the first aspect of the present invention consists essentially of and preferably consists entirely of the drug component and the propellant component. By the term "consists essentially of", we mean that at least 95 weight %, more preferably at least 98 weight % and especially at least 99 weight % of the pharmaceutical composition consists of the two listed components.

In one particularly preferred embodiment, the pharmaceutical composition of the first aspect of the present invention is also free of polar excipients such as ethanol. Polar excipients are used routinely in pharmaceutical compositions for treating respiratory disorders that are delivered using metered dose inhalers (MDIs). They are also referred to as solvents, co-solvents, carrier solvents and adjuvants. Their inclusion can serve to solubilise the surfactant or the drug in the propellant and/or inhibit deposition of drug particles on the surfaces of the metered dose inhaler that are contacted by the pharmaceutical composition as it passes from the container in which it is stored to the nozzle outlet. They are also used as bulking agents in two-stage filling processes where the drug is mixed with a suitable polar excipient. The most commonly used polar excipient is ethanol.

DETAILED DESCRIPTION

The present inventors have discovered that for salbutamol sulphate, the use of R-152a as the propellant mitigates the need for surfactants and polar excipients and allows compositions that are free of both surfactants and polar excipients to be prepared that still deliver good performance when delivered from a medication delivery device, such as a metered dose inhaler (MDI).

The majority of the drug will be dispersed or suspended in the propellant. The suspended drug particles preferably have a diameter of less than 100 microns.

The pharmaceutical composition of the first aspect of the invention typically comprises from 99.0 to 99.99 weight % of the R-152a-containing propellant and from 0.01 to 1.0 weight % of the salbutamol sulphate. Preferred compositions comprise from 99.5 to 99.95 weight % of the R-152a-containing propellant and from 0.05 to 0.5 weight % of the salbutamol sulphate. Particularly preferred compositions comprise from 99.8 to 99.93 weight % of the R-152a-containing propellant and from 0.07 to 0.2 weight % of the salbutamol sulphate. All percentages are based on the total weight of the pharmaceutical composition.

The drug component in the pharmaceutical composition of the invention consists of salbutamol sulphate. By the terms "consists of" and "consisting of" as used herein, we are intending to exclude the presence of additional components. Thus, the drug component in the pharmaceutical composition of the present invention consists entirely of salbutamol sulphate, so that the only drug in the pharmaceutical composition is salbutamol sulphate.

The propellant component in the pharmaceutical composition of the present invention consists essentially of 1,1-difluoroethane (R-152a). Thus, we do not exclude the possibility that the propellant component may include small amounts of propellant compounds in addition to the R-152a. For example, the propellant component may additionally comprise one or more additional hydrofluorocarbon or hydrocarbon propellant compounds, e.g. selected from R-227ea, R-134a, difluoromethane (R-32), propane, butane, isobutane and dimethyl ether. If an additional propellant compound is included, the R-152a will constitute at least 90 weight %, e.g. from 90 to 99 weight % of the propellant component. Preferably, the R-152a will constitute at least 95 weight %, e.g. from 95 to 99 weight %, and more preferably at least 99 weight % of the propellant component. In an especially preferred embodiment, the propellant component is entirely R-152a, so that the pharmaceutical composition of the invention comprises R-152a as the sole propellant.

It will be apparent from the discussion above, that in a preferred embodiment of the present invention, there is provided a pharmaceutical composition consisting of:
 a drug component consisting of salbutamol sulphate; and
 a propellant component consisting of 1,1-difluoroethane (R-152a).

The pharmaceutical composition of the invention finds particular utility in the delivery of the salbutamol sulphate from a pressurised aerosol container, e.g. using a metered dose inhaler (MDI). For this application, the pharmaceutical composition is contained in the pressurised aerosol container and the R-152a propellant functions to deliver the drug as a fine aerosol spray.

The pharmaceutical composition of the invention may comprise one or more other additives of the type that are conventionally used in drug formulations for pressurised MDIs, such as valve lubricants. Where other additives are included in the pharmaceutical composition, they are normally used in amounts that are conventional in the art.

The pharmaceutical composition of the invention is normally stored in a pressurised container or canister which is to be used in association with a medication delivery device. When so stored, the pharmaceutical composition is normally a liquid. In a preferred embodiment, the pressurised container is designed for use in a metered dose inhaler (MDI).

Accordingly, a second aspect of the present invention provides a pressurised container holding the pharmaceutical composition of the first aspect of the present invention. In a third aspect, the present invention provides a medication delivery device, especially a metered dose inhaler, having a pressurised container holding the pharmaceutical composition of the first aspect of the present invention.

In an especially preferred embodiment, the present invention provides a pressurised container holding a pharmaceutical composition consisting of:
 a drug component consisting of salbutamol sulphate; and
 a propellant component consisting of 1,1-difluoroethane (R-152a).

In another especially preferred embodiment, the present invention provides a medication delivery device, especially a metered dose inhaler, having a pressurised container holding a pharmaceutical composition consisting of:
 a drug component consisting of salbutamol sulphate; and a propellant component consisting of 1,1-difluoroethane (R-152a).

In the above especially preferred embodiments, the typical and preferred proportions of the drug and propellant components are as discussed above.

The pharmaceutical composition of the present invention is for use in medicine for treating a patient suffering or likely to suffer from a respiratory disorder and especially asthma.

Accordingly, the present invention also provides a method for treating a patient suffering or likely to suffer from a respiratory disorder, especially asthma, which comprises administering to the patient a therapeutically or prophylactically effective amount of a pharmaceutical composition as discussed above. The pharmaceutical composition is preferably delivered to the patient using a MDI.

The pharmaceutical composition of the invention can be prepared by a simple blending operation in which the salbutamol sulphate and the R-152a-containing propellant are mixed together in the required proportions in a suitable mixing vessel. Mixing can be promoted by stirring as is common in the art. Conveniently, the R-152a-containing propellant is liquefied to aid mixing. If the pharmaceutical composition is made in a separate mixing vessel, it can then be transferred to pressurised containers for storage, such as pressurised containers that are used as part of medication delivery devices and especially MDIs.

In a preferred embodiment, the pharmaceutical composition of the invention is prepared within the confines of a pressurised container, such as an aerosol canister or vial, from which the composition is ultimately released as an aerosol spray using a medication delivery device, such as a MDI. In this method, a weighed amount of the salbutamol sulphate is introduced into the open container. A valve is then crimped onto the container and the propellant, in liquid form, introduced through the valve into the container under pressure, optionally after first evacuating the container through the valve.

Once the desired components are in the container, the whole mixture can then be treated to disperse the drug in the propellant, e.g. by vigorous shaking or using an ultrasonic bath. Suitable canisters may be made of plastics, metal or glass.

Accordingly, in a forth aspect, the present invention provides a method for manufacturing a pharmaceutical composition, said composition consisting essentially of:
- a drug component consisting of salbutamol sulphate; and
- a propellant component consisting essentially of 1,1-difluoroethane (R-152a),
said method comprising the steps of:
- introducing a weighed amount of the drug component into an open container from which the drug component will ultimately be released as an aerosol spray using a medication delivery device;
- fitting a valve device onto the container; and
- introducing the propellant component, in liquid form, through the valve into the container under pressure.

After the introduction step, a mixing step is preferably conducted to mix the drug component into the propellant component. The mixing step helps to properly disperse the drug component in the pharmaceutical composition.

The preferred pharmaceutical compositions for use in the above method are as described above.

The container may be filled with enough of the pharmaceutical composition to provide for a plurality of dosages. The pressurized aerosol canisters that are used in MDIs, typically contain 50 to 150 individual dosages.

For pharmaceutical compositions that comprise a drug in suspension in a propellant, the problem can arise that the suspended drug particles deposit on the interior surfaces of the canister and the valve of the drug delivery device. This problem can necessitate providing the canister interior with a special lining or coating, such as a fluoropolymer coating, and making the valves from specialist polymer materials. However, by using R-152a as the propellant, this problem can be avoided for salbutamol sulphate.

The present invention is now illustrated but not limited by the following examples.

Example 1

A number of experiments were conducted to investigate the in vitro aerosolization performance of salbutamol sulphate in metered dose inhalers (MDIs) containing either R-134a or R-152a.

Drug-only formulations containing salbutamol sulphate were prepared in both R-134a and R-152a. The nominal dose of salbutamol sulphate was 100 μg. Drug was weighed directly into standard aluminium 19 mL cans (C128, Presspart, Blackburn, UK). The cans were then crimped with a 50 μL valve (Bespak, Kings Lynn, UK). Finally, the propellant was filled into the cans through the valve using a manual Pamasol crimper/filler (Pamasol, Switzerland).

High performance liquid chromatography (HPLC) was used to determine drug content following aerosolization studies (see below). The HPLC machine consisted of a pump, column oven, column coupled to a UV detector (all Agilent 1200, Wokingham, Berkshire, UK). A Hypersil BDS C18 column (Fisher, Loughborough, UK, 5 μm, 250×4.6 mm i.d.) was used for high-throughput analysis of samples. The chromatographic conditions are shown in Table 1 below.

TABLE 1

| Drug | Pump Flow Rate (ml·min$^{-1}$) | Mobile Phase | UV Wavelength (nm) | Column Temperature (°C.) |
|---|---|---|---|---|
| Salbutamol Sulphate (Sal SO$_4$) | 1.8 | Methanol:Water (0.25% W/V 1 - heptane sulfonic acid sodium salt) (40:60 V/V) | 240 | 60 |

The in vitro aerosolization performance of the formulations was studied using a Next Generation Impactor (NGI, Copley Scientific, Nottingham UK), which was connected to a vacuum pump (GE Motors, NJ, USA). Prior to testing, the cups of the NGI system were coated with 1% v/v silicone oil in hexane to eliminate particle bounce. For each experiment, three actuations of the can were discharged into the NGI at 30 L·min$^{-1}$ as per pharmacopeia guidelines. Following aerosolization, the NGI apparatus was dismantled and the actuator and each part of the NGI was washed down into known volumes of the HPLC mobile phase. The mass of drug deposited on each part of the NGI was determined by HPLC. This protocol was repeated three times for the can, following which, the fine particle dose (FPD) and fine particle fraction of the emitted dose (FPF$_{ED}$) were determined.

The in vitro aerosolization performance of salbutamol sulphate following aerosolization from MDIs using either R-134a or R-152a propellant is summarised in Table 2 and shown in FIG. 1. These data show that the emitted dose of salbutamol sulphate was significantly ($p<0.05$) greater when formulated with R-152a rather than R-134a. Furthermore, the mass median aerodynamic diameter (MMAD) of the salbutamol sulphate/R-152a formulation was smaller than the formulation of the drug with R-134a. These data show that the dispersion efficiency of the drug was better in R-152a than R-134a.

TABLE 2

| | Emitted Dose (µg ± S.D.) | Fine Particle Dose (µg ± S.D.) | $FPF_{ED}$ (%) | MMAD ± GSD |
|---|---|---|---|---|
| Salbutamol sulphate MDI (R-134a) | 75.6 (3.6) | 19.1 (3.3) | 25.6 (1.9) | 4.54 (2.76) |
| Salbutamol Sulphate MDI (R-152a) | 97.4 (4.8) | 25.55 (0.5) | 26.2 (0.4) | 3.41 (2.40) |

GSD = geometric standard deviation

Example 2

The suspension stability of salbutamol sulphate in propellant R-152a and propellant R-134a was investigated using a Turbiscan MA 2000 (Formulaction SA, France).

The Turbiscan instrument consists of a detection head, which moves up and down along a flat-bottomed cylindrical cell (FIG. 2). The detection head is composed of a pulsed near-infrared light source (L=850 nm) and two synchronous detectors. The transmission detector receives the light, which goes across the sample (at 180° from the incident beam), while the backscattering detector receives the light scattered backward by the sample (at 45° from the incident beam). The detection head scans the entire length of the sample (about 65 mm), acquiring transmission and back-scattering data each 40 mm (1625 transmission and backscattering acquisitions per scan). The integrated microprocessor software handles data acquisition, analogue-to-digital conversion, data storage, motor control and computer dialogue.

Weighed amounts of salbutamol sulphate were introduced into 14 mL pressure-resistant, clear glass aerosol bottles. The bottles were then crimped with a continuous valve (Bespak, Kings Lynn, UK), following which either R-152a or R-134a was filled into the glass bottles through the valve using a manual Pamasol crimper/filler (Pamasol, Switzerland). The total weight of each formulation prepared was 10 g and the amount of salbutamol sulphate and propellant in the formulations is shown in Table 3 below. Finally, each bottle was sonicated for 20 minutes to aid dispersion of the drug in the suspension.

TABLE 3

| Propellant | Weight of Drug (g) | Weight of Propellant (g) |
|---|---|---|
| HFA 134a | 0.0164 | 9.984 |
| HFA 152a | 0.0220 | 9.978 |

Prior to analysis using the Turbiscan instrument, the clear glass bottles containing the salbutamol sulphate/propellant formulations were vigorously shaken in order to thoroughly disperse the drug in the formulations. The glass bottles were then loaded into the Turbiscan head. Analysis of the samples was carried out over a 5 minute period to determine at which point sedimentation of the salbutamol sulphate occurred.

When R-152a was used as the propellant, it took 2 minutes for the salbutamol sulphate to sediment. In contrast, the salbutamol sulphate took less than 30 seconds to sediment when R-134a was used as the propellant. The longer sedimentation time with R-152a propellant is highly advantageous, because it allows the drug to remain properly dispersed throughout the propellant following shaking for a longer period of time. This, in turn, provides greater certainty that the drug is properly dispersed in the propellant when the MDI is operated to expel the drug formulation and hence greater certainty that the drug is delivered properly into the lung.

The better suspension performance of salbutamol sulphate in R-152a is also completely unexpected given that R-152a, which has a density of 0.9 g/cm$^3$, is much less dense than R-134a, which has a density of 1.22 g/cm$^3$.

What is claimed is:

1. A surfactant-free pharmaceutical composition consisting essentially of:
    (a) a drug component consisting of salbutamol sulphate; and
    (b) a propellant component consisting essentially of 1,1-difluoroethane (R-152a).

2. The pharmaceutical composition of claim 1 which is free of polar excipients.

3. The pharmaceutical composition of claim 1 which is free of ethanol.

4. The pharmaceutical composition of claim 1, wherein the propellant component consists entirely of R-152a.

5. The pharmaceutical composition of claim 1 which consists entirely of components (a) and (b).

6. A sealed container that contains a pharmaceutical composition as claimed in claim 1.

7. The sealed container of claim 6 which is a pressurized container for use with a metered dose inhaler (MDI).

8. A metered dose inhaler (MDI) fitted with a pressurized container as claimed in claim 7.

9. A method for treating a patient suffering or likely to suffer from a respiratory disorder which comprises administering to the patient a therapeutically or prophylactically effective amount of a pharmaceutical composition as claimed in claim 1.

10. The method of claim 9, wherein the respiratory disorder is asthma.

11. The method of claim 9, wherein the pharmaceutical composition is delivered to the patient using a metered dose inhaler (MDI).

12. A method for manufacturing a pharmaceutical composition as claimed in claim 1, said method comprising the steps of:
    introducing a weighed amount of the drug component into an open container from which the drug component will ultimately be released as an aerosol spray using a medication delivery device;
    fitting a valve device onto the container; and
    introducing the propellant component, in liquid form, through the valve into the container under pressure.

* * * * *